(12) United States Patent
Galeone et al.

(10) Patent No.: US 8,715,702 B2
(45) Date of Patent: May 6, 2014

(54) DEPOSITION OF LIPOPHILIC ACTIVE MATERIAL IN SURFACTANT CONTAINING COMPOSITIONS

(75) Inventors: Fabrizio Galeone, Buvrinnes (BE); Lorry Deklippel, Piéton (BE); Leon Andre Marteaux, Brussels (BE); Stephane Ugazio, Soignies (BE)

(73) Assignee: Dow Corning Corporation, Midland, MI (US)

( * ) Notice: Subject to any disclaimer, the term of this patent is extended or adjusted under 35 U.S.C. 154(b) by 664 days.

(21) Appl. No.: 12/919,286

(22) PCT Filed: Feb. 25, 2009

(86) PCT No.: PCT/EP2009/001349
§ 371 (c)(1),
(2), (4) Date: Dec. 15, 2010

(87) PCT Pub. No.: WO2009/106318
PCT Pub. Date: Sep. 3, 2009

(65) Prior Publication Data
US 2011/0104221 A1 May 5, 2011

(30) Foreign Application Priority Data

Feb. 27, 2008 (GB) .................................. 0803538.8

(51) Int. Cl.
*A61K 8/11* (2006.01)
*C11D 3/50* (2006.01)

(52) U.S. Cl.
USPC ............... 424/401; 510/516; 510/535; 8/137; 512/4

(58) Field of Classification Search
CPC combination set(s) only.
See application file for complete search history.

(56) References Cited

U.S. PATENT DOCUMENTS

| | | | |
|---|---|---|---|
| 4,152,272 A | 5/1979 | Young | |
| 5,035,832 A | 7/1991 | Takamura et al. | |
| 5,094,761 A | 3/1992 | Trinh et al. | |
| 5,102,564 A | 4/1992 | Gardlik et al. | |
| 5,207,933 A | 5/1993 | Trinh et al. | |
| 5,232,612 A | 8/1993 | Trinh et al. | |
| 5,234,610 A | 8/1993 | Gardlik et al. | |
| 5,234,611 A | 8/1993 | Trinh et al. | |
| 5,236,615 A | 8/1993 | Trinh et al. | |
| 5,506,201 A | 4/1996 | McDermott et al. | |
| 6,042,792 A | 3/2000 | Shefer et al. | |
| 6,051,540 A | 4/2000 | Shefer et al. | |
| 6,251,313 B1 | 6/2001 | Deubzer et al. | |
| 6,303,149 B1 | 10/2001 | Magdassi et al. | |
| 6,855,335 B2 | 2/2005 | Scok et al. | |
| 7,119,060 B2 | 10/2006 | Shefer et al. | |
| 2004/0256748 A1 | 12/2004 | Scok et al. | |
| 2006/0039934 A1 | 2/2006 | Ness et al. | |
| 2006/0217288 A1* | 9/2006 | Wahl et al. ..................... 510/515 |

FOREIGN PATENT DOCUMENTS

| | | |
|---|---|---|
| EP | 0346034 A2 | 12/1989 |
| EP | 0469228 A1 | 2/1992 |
| EP | 0617051 A2 | 9/1994 |
| EP | 0934773 A2 | 8/1999 |
| EP | 0941761 A2 | 9/1999 |
| FR | 2858637 A1 | 2/2005 |
| GB | 2416524 A | 2/2006 |
| JP | 63122796 A | 5/1988 |
| WO | WO 98/28396 A1 | 7/1998 |
| WO | WO 01/80823 A2 | 11/2001 |
| WO | WO 03/066209 A1 | 8/2003 |
| WO | WO 2005/009604 A1 | 2/2005 |
| WO | WO 2006/088980 A1 | 8/2006 |
| WO | WO 2007/000316 A1 | 1/2007 |
| WO | WO 2007/038570 A1 | 4/2007 |
| WO | WO 2007/100501 A2 | 9/2007 |

OTHER PUBLICATIONS

English language abstract for EP 0941761 extracted from espacenet.com database, dated Dec. 20, 2010, 9 pages.
English language abstract for FR 2858637 extracted from espacenet.com database, dated Dec. 20, 2010, 12 pages.
English language abstract for JP 63-122796, extracted from CAPLUS and MEDLINE database, 13 pages, 1988.
PCT International Search Report for PCT/EP2009/001349, dated Nov. 9, 2010, 3 pages.
Dr. Alan Rawle, Technical Update "Basic Principles of Particle Size Analysis", Rawle, A. Malvern Instruments Ltd, Malvern, Worcestershire, UK. Surface Coatings International, Part A: Coatings Journal (2003), 8 Pages; Publisher: SURFEX Ltd., CODEN: SCIPCT ISSN: 1476-4857. Journal; General Review written in English. CAN 140:43547 AN 2003:285586 CAPLUS.

* cited by examiner

*Primary Examiner* — Sue Liu
*Assistant Examiner* — Jessica Kassa
(74) *Attorney, Agent, or Firm* — Howard & Howard Attorneys PLLC

(57) ABSTRACT

The present invention relates to a controlled release carrier system that can be incorporated into rinse-off application products containing at least one surfactant such as heavy duty liquids (HDL), Rinse Cycle Fabric Softeners (RCFS), Shampoos, Hair Conditioners, Shower Gels, cleansing products, and that enhance deposition of lipophilic active materials like fragrance, fine perfumes, flavors and other volatile compounds onto a surface. The fragrance composition is encapsulated within a shell comprising a silicon-containing material and the shell has a mean diameter size which is lower than 30 micrometer. The surfactant composition containing the fragrance composition is washed off and the fragrance is progressively released.

13 Claims, No Drawings

US 8,715,702 B2

DEPOSITION OF LIPOPHILIC ACTIVE MATERIAL IN SURFACTANT CONTAINING COMPOSITIONS

RELATED APPLICATIONS

This application claims priority to and all the advantages of International Patent Application No. PCT/EP2009/001349, filed on Feb. 25, 2009, which claims priority to Great Britain Patent Application No. GB 0803538.8, filed on Feb. 27, 2008.

FIELD OF THE INVENTION

The present invention relates to a controlled release carrier system that can be incorporated into rinse-off application products containing at least one surfactant such as heavy duty liquids (HDL), Rinse Cycle Fabric Softeners (RCFS), Shampoos, Hair Conditioners, Shower Gels, cleansing products, and that enhance deposition of lipophilic active materials like fragrance, fine perfumes, flavours and other volatile compounds onto a surface.

This invention also relates to surfactant based compositions with improved lipophilic active material deposition and use thereof.

BACKGROUND TO THE INVENTION

A significant problem with current surfactant containing formulations used in wash off application is the poor deposition of lipophilic actives materials onto the surfaces to be treated. Typical fabric care products such as laundry detergent compositions and fabric softener compositions contain 0.5% to 1% by weight fragrance.

U.S. Pat. No. 6,051,540 disclose that the amount of fragrance left as a residue on the clothes can be as low as 1% of the original amount of fragrance in the starting product.

Without being bound by theory, it is believed that the lipophilic (oil) active material in general and fragrance in particular is rapidly solubilised by the surfactant micelles in the so called micellisation process. As a result of this micellisation process only a few part of active material is depositing on the surfaces to be treated. Most of the lipophilic active material is washed off in the rinsing water; see for example the article by Yoshikazu Tokuoka et al. (Langmuir 1995, 11, 725-729) dealing with the solubilisation of some synthetic perfumes by anionic-nonionic mixed surfactant systems.

A classical method for enhancing fragrance deposition is admixing the fragrance with surfactants and especially with cationic surfactants contained in conditioner compositions. An alternative route involves the preparation of solid particles by admixing the fragrance with amphiphilic polymers for example as described in EP-A 0 469 228.

U.S. Pat. No. 4,152,272 and EP-A 0 346 034 show incorporation of perfume into wax particles.

U.S. Pat. No. 5,506,201 discloses a method for producing a fragrance-containing solid particle of improved substantivity for incorporation into laundry detergents which comprises of a fat component and a solid surface active agent like sorbitan ester.

U.S. Pat. No. 6,042,792 describes bioactive compositions for targeted delivery to skin, hair and fabric in solid solution in a wax or polymer matrix.

US2004/0256748 (Seok) describes a process for preparing silica microcapsules comprising the steps of dissolving tetraethyl orthosilicate (TEOS) into an aqueous solution containing a hydrolysis catalyst to control a degree of hydrolysis and contribute hydrophilicity or lipophilicity, adding a core material and an appropriate amount of aminopropyltrialkoxysilane (APS) as a gelling agent into the solution, and emulsifying and dispersing the resulting solution to a solution having a polarity opposite to that of the core material to microcapsulate by coating the core material with silica shell via a sol-gel reaction. In example 8 it is claimed that a liposoluble perfume is encapsulated.

FR2858637 describes a textile article containing microcapsules with shells in melamine or polydimethylsiloxane, the active product can be a perfume. The encapsulation is typically made by in situ polymerisation.

GB2416524 describes another in-situ polymerisation process where a lipophilic cosmetic, chemical, biological or pharmaceutical active material composition is encapsulated by mixing it with a water reactive silicon compound and emulsifying the mixture in an aqueous medium under shear and in the presence of at least one surfactant, thereby forming an aqueous suspension of microcapsules having a core of the active material composition surrounded by a shell of siliconbased network polymer. The polysiloxane shell is preferably made by condensation of a tetraalkoxy- or trialkoxy-alkylsilane such as tetraethoxysilane (TEOS). The preferred active material is a sunscreen.

WO2005/009604 describes a method for preparing microcapsules where an oily phase comprising a water insoluble precursor and the core material is emulsified in water. Then appropriate shear and temperature conditions are applied to form the microcapsules.

According to sol-gel or in-situ polymerisation processes described before, a precursor such as TEOS and an active ingredient are directly mixed together, emulsified in presence of a low amount of water then TEOS is polymerised in-situ. On the contrary, in a core-shell process, an aqueous emulsion of active ingredient is first made, then TEOS is added in the continuous aqueous phase under shear and an "ex-situ" polymerisation is conducted. As shown in the examples of the present description, microcapsules obtained by sol-gel or process tend to be of lower stability than core-shell microcapsules.

BRIEF DESCRIPTION OF THE INVENTION

We now found that the core shell encapsulation of oil active material by a silicate shell can prevent their micellisation by surfactant contained in the formulation. As a consequence of that, significantly improved deposition of the lipophilic active material onto surfaces in wash off applications has been observed.

In the present specification, the term "silicate shell" refers to a shell material obtained from a silicon-containing material, preferably a silicon-containing material obtained from the hydrolysis and condensation of alkoxysilanes.

In the present specification the term "lipophilic active material" refers to olfactive components like fragrances, odour masking agents and mixtures thereof such as perfume compositions as well as precursors for the above. In the following description, the term fragrance is used to indicate any material or composition containing a lipophilic olfactive compound or precursor.

This active material is usually a formulation of various olfactive molecules such as delta & beta damascone, benzaldehyde, benzyl acetate, verdyl acetate, hexyl cinnamic aldehyde, aldehyde: $C_8$, $C_{10}$, $C_{11}$ undecylenic, $C_{12}$ lauric, $C_{12}$ MNA, ionone beta, bangalol, manzanate, OTBCA, iso E super, tetra hydro Linalol, phenyl ethyl 2 phenylacetate 2, menthol, linalol, linalyl acetate, camphor, eucalyptol, terpinyl acetate, kephalis, ambrofix, indole anethole sandalore, vanillin, coumarine eugenol, lilal, hydroxycitronellal, methyl pamplemousse, geranitrile, hedione, jasmine cis, fixolide, galaxolide, methym anthranilate, geraniol, citronellol, gardenol, tricydal, phenyl ethyl alcohol, phenyl acetaldehyde, pyralone, calone, natural oils from: lavender, lavandin grosso, rosemary, eucalyptus, artesimia, clary sage, star anise, basil, cumin, citronella, lemongrass, lemon, bergamot yellow mandarin, orange, lime, ylang ylang, galbanum, marigold, peppermint, spearmint, neroli, petitgrain, orange flowers, olibanum, rose, geranium, cassia, nutmeg, black pepper, juniper, coriander, sandalwood, cedarwood, vetyver, patchouli, oakmoss, pine, focus, celery seeds, carrot seeds and abstracts from: civet, peru balsam, vanilla, tonka beans, cistus, jasmine, tuberose, mimosa, blackcurrant buds, osmanthus, violet leaves, orange flowers and rose de mai but is not limited to this list of compounds.

The term "microcapsule" means a capsule having a particle size of up to 1 mm, thus it includes microcapsules having a particle size of 1 micrometer to 1 mm and nanocapsules having a particle size less than 1 micrometer.

Examples of rinse off application can be laundry, fabric softening, hair washing, hair conditioning, cleansing, shower cleaning etc.

DESCRIPTION OF RELATED ART

Several Core-Shell Microcapsules suspensions and various processes of making core-shell microcapsules are described in EP 0934773, EP 0941761, U.S. Pat. No. 6,303,149, WO 03/066209, WO-A-2005/009604 and GB 2416524. WO 03/066209 mentions that fragrance or perfume can be encapsulated.

Micro-encapsulation and inclusion complexes with cyclodextrines have been used to decrease volatility, improve stability and provide slow-release properties. However, cyclodextrines poured into water release the fragrance immediately, which limits their uses as controlled release systems in e.g. laundry care, for example U.S. Pat. No. 5,094,761 5,207,933 5,232,612, 5,234,611, 5,236,615, 5,102,564, and 5,234,610.

U.S. Pat. No. 7,119,060 discloses a controlled delivery system (CDS) that can be incorporated in liquids as well as, dry granular, or powder, fabric care products, such as fabric softeners, laundry detergents, rinse added products, and other fabric care product to enhance fragrance performances. The CDS is a solid substantially spherical particle comprising hydrophobic cationic charge enhancing agents in conjunction with cationic fabric softening agents that assist in adhering the particles onto fabric. The particles are matrix type microcapsules and the polymers forming the matrix are hydrophobic.

Perfume enhanced deposition has been described through incorporation into latexes during the polymerisation process, for example in EP-A 0 617 051, JP-A 63/122796 and WO 98/28396.

DETAILED DESCRIPTION OF THE INVENTION

This invention provides compositions containing at least one surfactant and core-shell microcapsules having a lipophilic active material core and a shell, preferably a silicate or silicon-containing polymeric shell, used in rinse-off application. The active material is a perfume or a fragrance which is released when the microcapsules are broken.

WO 03/066209 explains in its paragraph 19 that when a perfume is encapsulated, the shell must be breakable to release the perfume. Therefore, large particles of diameter of at least 10 micrometer, for example 50 micrometer or above are preferred as they are more readily breakable than smaller particles. Similarly, U.S. Pat. No. 7,119,060 in its column 8 states: "the permeation rate of the fragrance from the particle is proportional to particle size such that the smaller particles, the faster the rate that fragrance that is being released. ( . . . ) Preferably the particle size of the fragrance-containing particles is in the range from about 50 microns to 200 microns."

Thus it was believed that large core-shell particles are more able to provide breakable shells releasing the perfume. On the contrary, we have surprisingly found that a better fragrance diffusive effect can be obtained with microparticles of a small size.

Preferably, the microcapsules have a mean diameter size lower than 30 micrometer, preferably lower than 20 micrometer, for example in the range of 0.5 to 20 micrometer, more preferably in the range between 1 and 10 micrometer, for example in the range of 1.5 to 7 micrometer.

The diameter size of the microcapsules can be estimated with a microscope, for example by examining samples under a scanning electron microscope (SEM).

Microcapsules Shell Thicknesses are preferably determined by the following physical relationships:

$$\text{Shell Thickness(nm)} = ((Dv0.5/2) - (Dv0.5/2*(\text{Payload}/100)^{1/3}))*1000$$

With:

Dv 0.5 expressed in micrometer.

Payload=Volume Core material*100/(Volume Core material+Volume shell)

Volume Core material=Weight Core Material/Density of Core Material

Volume shell=Weight shell/2

Particle size measurements here specified are made by laser diffraction technique using a "Mastersizer 2000" from Malvern Instruments Ltd., UK, and further information on the above particle sizes can e.g. be found in "Basic principles of particle size analytics", Dr. Alan Rawle, Malvern Instruments Limited, WR14 1XZ, UK and the "Manual of Malvern particle size analyser". Particular reference is made to the user manual number MNA 0096, Issue 1.0, November 1994. All particle sizes indicated in the present application are mean average particle size according to D (v, 0.5) and are measured with a Malvern Mastersizer, if nothing else is stated or obvious.

Preferably, the particle size distribution is small, for example at least 80% of the particles have a Dv comprised between 50 and 200% of the Dv 0.5 value. For example, microcapsules have Dv 0.1=5 micrometer, Dv 0.5=10 micrometer and Dv 0.9=20 micrometer.

A deposition aid material can be used in conjunction with the core-shell microcapsules to improve the deposition of the core-shell microcapsules onto targeted surfaces. Preferably, the deposition aid material is cationic. One preferred class of materials is cationic guar gum derivatives such as guar hydroxypropyltriammonium chloride (which is commercially available from Rhodia under the Trade Mark Jaguar). Particularly preferred is Jaguar C13S, which has a low degree of substitution of the cationic groups and high viscosity. Other deposition aids useful for the present invention are:

Quaternary ammonium compounds
Polyvinyl amines
Polyalkyleneimines
Poly-quaternary ammonium compounds.

According to one aspect of the present invention, an aqueous suspension of an encapsulated fragrance composition is provided, which comprises microcapsules having a core of the fragrance composition surrounded by a shell of a silicon-based network polymer, characterised in that the weight ratio of the fragrance composition in the microcapsules to the silicon-based network polymer shell is at least 1.5:1 and the suspension contains a cationic or amphoteric surfactant.

We use the term "emulsion" to mean a liquid in liquid dispersion and "suspension" to mean a solid in liquid dispersion. Therefore we consider the dispersion of microcapsules as a suspension. It should be understood however that, when looking at the final dispersion, it may be visually difficult or impossible to differentiate a suspension from an emulsion.

Preferably, a tetraalkoxysilane compound is used in making the shell of the microcapsules. A tetraalkoxysilane such as tetraethoxysilane (TEOS) can be used in monomeric form or as a liquid partial condensate. The tetraalkoxysilane can be used in conjunction with one or more other water-reactive silicon compound having at least two, preferably at least 3, Si—OH groups or hydrolysable groups bonded to silicon, for example an alkyl trialkoxy silane such as methyl trimethoxy silane or a liquid condensate of an alkyl trialkoxy silane. Hydrolysable groups can for example be alkoxy or acyloxy groups bonded to silicon. The alkyl and alkoxy groups in the tetraalkoxysilanes or other silanes preferably contain 1 to 4 carbon atoms, most preferably 1 or 2 carbon atoms. The tetraalkoxysilane and other water-reactive silicon compound if used, hydrolyses and condenses to form a network polymer, that is a 3-dimensional network of silicon-based material, around the emulsified droplets of the lipophilic active material composition. The water-reactive silicon compound preferably consists of at least 50%, more preferably at least 75%, and most preferably 90-100% tetraalkoxysilane. We have found that a tetraalkoxysilane can be the most effective silicon compound for forming impermeable microcapsules, forming a 3-dimensional network consisting substantially of $SiO_{4/2}$ units.

Small particle size can be favoured for instance by increasing shear, cavitation or pressure during the emulsification process. Other means favouring a small oil droplet size can be used, as will appear from the following description.

The fragrance composition is a liquid at the time it is emulsified and usually is liquid at ambient temperature. It can be an undiluted liquid active material or can be a solution containing at least one fragrance in a lipophilic solvent, preferably a non-volatile solvent, or a water-in-oil emulsion, or a lipophilic suspension. Solid active fragrance materials can be melted before being emulsified if their melting temperature is significantly below 100° C.

The lipophilic active material composition is emulsified in an aqueous medium preferably with the aid of a surfactant.

The surfactant is most preferably a cationic or amphoteric surfactant, which readily forms an emulsion of positive zeta-potential. We have found that a positive zeta-potential promotes condensation and polymerisation of the tetraalkoxysilane at the interface of the emulsified droplets of the lipophilic active material composition, leading to more impervious microcapsules. Nonionic surfactants can be used; for example the cationic or amphoteric surfactant can be mixed with up to an equal weight of nonionic surfactant.

The concentration of surfactant in the aqueous emulsion of lipophilic active material can be between 0.01 and 10% by weight, but is preferably at least 0.02% and below 2%, most preferably 0.05 to 1.5% by weight of the emulsion, particularly 0.2-1.0%. In general the use of low levels of surfactant during emulsification of the lipophilic active material and reaction with the alkoxysilane leads to microcapsules which are more resistant to diffusion or leaching of the lipophilic active material from the microcapsules.

Subsequent addition of surfactant to the suspension of microcapsules has less or no effect on diffusion or leaching of the lipophilic active material from the microcapsules.

The weight ratio of oil phase to aqueous phase in the emulsion can generally be between 40:1 and 1:50, although the higher proportions of aqueous phase are economically disadvantageous particularly when forming an emulsion of microcapsules. Usually the weight ratio of oil phase to aqueous phase is between 2:1 and 1:3. If the active material composition is highly viscous, a phase inversion process can be used in which the oil phase is mixed with surfactant and a small amount of water, for example 2.5 to 10% by weight based on the oil phase, forming a water-in-oil emulsion which inverts to an oil-in-water emulsion as it is sheared. Further water can then be added to dilute the emulsion to the required concentration.

Examples of cationic surfactants include quaternary ammonium hydroxides such as octyl trimethyl ammonium hydroxide, dodecyl trimethyl ammonium hydroxide, hexadecyl trimethyl ammonium hydroxide, octyl dimethyl benzyl ammonium hydroxide, decyl dimethyl benzyl ammonium hydroxide, didodecyl dimethyl ammonium hydroxide, dioctadecyl dimethyl ammonium hydroxide, tallow trimethyl ammonium hydroxide and coco trimethyl ammonium hydroxide as well as corresponding salts of these materials, fatty amines and fatty acid amides and their derivatives, basic pyridinium compounds, quaternary ammonium bases of benzimidazolines and polypropanolpolyethanol amines. Cationic emulsions of microcapsules have increased deposition of the microcapsules from the emulsion and increased substantivity on both hair and skin.

Examples of suitable amphoteric surfactants include cocamidopropyl betaine, cocamidopropyl hydroxysulfate, cocobetaine, sodium cocoamidoacetate, cocodimethyl betaine, N-coco-3-aminobutyric acid and imidazolinium carboxyl compounds.

The above surfactants may be used individually or in combination.

Examples of non-ionic surfactants include polyoxyalkylene alkyl ethers such as polyethylene glycol long chain (12-14C) alkyl ether, polyoxyalkylene sorbitan ethers, polyoxyalkylene alkoxylate esters, polyoxyalkylene alkylphenol ethers, ethylene glycol propylene glycol copolymers, polyvinyl alcohol and alkylpolysaccharides, for example materials of the structure RI—O—(R2O)m-(G)n wherein Ri represents a linear or branched alkyl group, a linear or branched alkenyl group or an alkylphenyl group, R2 represent an alkylene group, G represents a reduced sugar, m denotes 0 or a positive integer and n represent a positive integer as described in U.S. Pat. No. 5,035,832.

The continuous phase of the emulsion can be a mixture of water with a water-miscible organic solvent such as an alcohol or lactam provided that the continuous phase is not miscible with the lipophilic active material. The particle size of the emulsion of lipophilic active material can be reduced before addition of the water-reactive silicon compound, for example in an apparatus applying increased shear such as a homogeniser or microfluidiser, or a sonolator (ultrasonic mixer). The emulsion can alternatively be prepared by phase inversion.

The particle size of the microcapsules produced generally corresponds to the particle size of the starting emulsion and can for example be in the range 0.1 to 30 micrometer.

The aqueous phase of the emulsion preferably contains a thickener, for example polyvinylpyrrolidone, polyvinyl alcohol, bentonite clay, a cellulose derivative, particularly a cellulose ether such as sodium carboxymethylcellulose, a lightly crosslinked acrylic polymer, modified starch, an alginate or xanthan gum, to inhibit settling of the microcapsules from the emulsion during formation or subsequently. The thickener is added to the emulsion before addition of the tetraalkoxysilane. Addition of polyvinylpyrrolidone to the emulsion before addition of the tetraalkoxysilane promotes formation of microcapsules more resistant to diffusion of the lipophilic material from the microcapsules for most particle sizes of the microcapsules.

The tetraalkoxysilane, and other water reactive silicon compound if used, can be added to the emulsion of active material composition as an undiluted liquid or as a solution in an organic solvent or in an emulsion form. The tetraalkoxysilane and the emulsion are generally mixed under shear during addition and subsequently during condensation to form the silicon-based polymer shell on the surface of the emulsified droplets. Mixing can for example be by stirring, but it is preferred that the emulsion and the tetraalkoxysilane are subjected to high shear, for example in a mixer of the rotor and stator type such as a Silberson (trade mark) mixer, either during addition of the tetraalkoxysilane or after addition of the tetraalkoxysilane and before formation of microcapsules is complete.

High shear mixing immediately after addition of the tetraalkoxysilane is preferred. This leads to microcapsules of reduced particle size and appears to promote polymerisation of substantially all the tetraalkoxysilane at the interface of the emulsion droplets.

The condensation reaction can be conducted at acidic, neutral or basic pH. The condensation reaction is generally carried out at ambient temperature and pressure, but can be carried out at increased temperature, for example up to 95° C., and increased or decreased pressure, for example under vacuum to strip the volatile alcohol produced during the condensation reaction. The weight ratio of active material composition to water reactive silicon compound is preferably at least 0.5:1 and in many cases may be at least 1.5:1, for example 2:1 to 9:1. Smaller microcapsules, for example those formed from a microemulsion, generally have a lower ratio of active material composition to water reactive silicon compound.

For many uses it may be preferred to recover the microcapsules from suspension, for example for subsequent dispersion in a different medium. An encapsulated fragrance can for example be dispersed in a water based preparation, preferably in such a proportion that the content of fragrance in the preparation is 0.1 to 10% by weight. Alternatively the microcapsules can be redispersed in an organic solvent, optionally with additives such as surfactant and/or polymer. Recovery of the microcapsules can be achieved by any known liquid removal technique, for example by spray drying, spray chilling, filtering, oven drying or lyophilisation.

The encapsulated product can be post-treated with a water-reactive metal alkoxy or acyloxy compound. The metal compound should be gradually hydrolysed in water rather than immediately reacting with water; compounds of Group IVB, IVA or VA of the Periodic Table are suitable such as compounds of silicon, titanium, zirconium or vanadium. The water-reactive metal alkoxy or acyloxy compound can for example harden the shell of the microcapsules and/or make them more impermeable. The reactive metal alkoxy or acyloxy compound can for example be an alkoxysilane or acyloxysilane, particularly a trialkoxysilane such as methyl triethoxy silane or isobutyl triethoxy silane, or a silane having Si—H functionality such as tris(dimethylhydrogensilyloxy) n-octyl silane, or alternatively a titanium alkoxide(alkyl titanate).

The reactive metal alkoxy or acyloxy compound can have an organic functional group to promote adhesion to substrates, especially textile substrates, for example 3-methacryloxypropyl trimethoxy silane, 3-aminopropyl triethoxysilane, 3-aminopropyl trimethoxy silane, 3-glycidoxypropyl trimethoxy silane and 3-(2-aminoethylamino)propyl trimethoxy silane. The microcapsules can be post-treated with a reactive metal alkoxy or acyloxy compounds, e.g. an alkoxysilane to change their physical and/or chemical properties, for example by making the capsule surface more hydrophobic or more hydrophilic. For example, the microcapsule surface can be made more hydrophobic by reaction with a silane having a long chain alkyl group such as octyl triethoxy silane. As an alternative to chemical reaction the microcapsules can be coated with a material which alters their surface properties. The surface treatment can be carried out on the microcapsules in suspension or on the separated solid microcapsules.

When encapsulating fragrance, a controlled rate of release may be preferred, and this can be achieved by adjusting the level of surfactant, the level of tetraalkoxysilane and optionally of trialkoxysilane, and the particle size.

The invention provides a fragrance carrier system comprising an encapsulated fragrance composition, wherein the fragrance composition is encapsulated within a shell comprising a silicon-containing material and the shell has a mean diameter size which is lower than 30 micrometer. Preferably, the shell has a mean diameter size lower than 20 micrometer. More preferably, the shell has a mean diameter size of at least 0.5 micrometer. For example, the shell has a mean diameter size comprised between 1 and 10 micrometer, more preferably the shell has a mean diameter size comprised between 1.5 and 7 micrometer.

The shell is preferably a polymerisation product of one or more alkoxysilane compound, preferably an emulsion polymerisation product of a tetraalkoxysilane.

The invention also provides a surfactant containing composition containing the fragrance carrier system, hereinafter called "surfactant composition" for instance a rinse-off composition. The surfactant composition can be selected from a fabric softener, liquid laundry detergent, rinse added product, drier-added fabric softener product, ironing added product, hair conditioner, shampoo, soap, dish-washing product and shower gel. Preferably, the surfactant composition contains a deposition aid material preferably chosen from at least one of: quaternary ammonium compounds, polyvinyl amines, polyalkyleneimines and poly-quaternary ammonium compounds. More preferably, the deposition aid material is a cationic guar gum derivative preferably a guar hydroxypropyltriammonium halide.

The invention also provides a process to deliver a fragrance to a substrate, wherein the substrate is treated by a surfactant composition as described above, the surfactant composition is washed off and the fragrance is progressively released.

EXAMPLES

Washing machine test and panel test for perfume delivery assessment: (European washing machine)

4 towels and 5 pillow cases (1 kg in total) are first washed (with a commercial detergent powder at 95° C., then without detergent powder at 95° C., then with detergent powder at 95° C., and finally without detergent powder at 95° C.) to remove the surface treatment. These pieces of fabrics will be used as a load for the wash cycle.

Fabric Treatment:
  Load: 4 small towels and 5 pillow cases (1 kg in total) are placed alternatively (a pillow case, a small towel, a pillow case) in the washing machine.
  Detergent:
   Add liquid detergent HDL1 (see the composition below) in a dosing ball which is then placed in approximately the middle of the washing machine (Miele W934). When RCFS is tested, liquid detergent HDL1 without perfume is used and perfumed RCFS is added in the machine drawer.
  Wash program: short washing program, at 40° C., rinse, spinning speed: 600 rpm, manual addition of 12 liters of soft water.
  Line dry the towels for 24 hours.
  After drying, fold the towels and put them on the shelves the panel can then start to evaluate the perfume intensity.
Panel Test:
  The panel test is only run using the towels. The pillow cases are not tested; they are used as a load only.
  Right after the wash cycle, the perfume intensity from wet towels is evaluated.
  Compare at least 2 towels per series and classified in descending order.
  Each series needs to be smelled on a daily base for at least a week.
  The towels are replaced every day. For instance the towel which has been used first is replaced by a second towel taken from the bottom of the pile and the first used towel is placed on the top of the pile formed by the remaining towels. For the third day the towel placed at the bottom of the pile will replace the towels which have been used by the panellists during day 2.
  The perfume delivered either from a liquid detergent or from a rinse cycle fabric softener here are the composition of these 2 products:
  HDL1 Composition:

| Dehydol LT 7 | 7.3% (w/w) |
| Maranil Pasta 55 | 17.7% (w/w) |
| Water | Q.S. |

RCFS: it contains 16% of Ester-quat (LT1 from Kao). 12 g of this formulation containing a defined amount of perfume is added to the rinse cycle drawer.

The application is illustrated by the following examples. These examples are illustrative and are not intended to limit the scope of the invention in any way.

Example 1

35.01 g of d-Damascone (delta-Damascone) (BLH) was emulsified in 64.39 g water containing 0.20 g Pareth-3 non-ionic polyethylene glycol lauryl ether surfactant and 0.11 g cetyl trimethyl ammonium chloride (CTAC) cationic surfactant. The coarse emulsion was emulsified by a rotor/stator mixer IKA Ultra-Turax T 25 Basic at 13500 rpm during 90 seconds. 5% TEOS was added to the emulsion while stirring to form a coarse emulsion of microcapsules. Microcapsules of average volume particle size (Dv 0.5) 4.4 micrometers (μm) were produced in suspension and the shell thickness was 13.9 nm.

The suspension was added and mixed with propeller at 300 rpm during 30 minutes to 55 g of a heavy liquid detergent (HDL 1) to get an encapsulated d-Damascone concentration of 0.75% (w/w). This composition was left standing at rest for 24 hrs.

The washing was carried out according to the procedure described above.

Eight panellists over 9 found more intensive scent from d-Damascone microcapsules treated wet towel vs. neat d-Damascone treated wet towels (control).

Example 2

Following the procedure described in the example 1, d-Damascone was encapsulated and placed into a liquid detergent (HDL1) together with some Jaguar C13S to get a perfume concentration of 1.5%.

This formulation was then compared to a liquid detergent only containing 1.5% free perfume.

| | Microcapsules Dv 0.5 (μm) | Results wet | Results after 1 day | Results after 2 days | Results after 3 days |
| --- | --- | --- | --- | --- | --- |
| Example 2 | 5.2 | 5/5 | 19/28 | 29/38 | 9/23 |

When the towels were wet and until after 2 days of storage most of the panellists recognised that the perfume intensity was higher when the perfume is encapsulated.

Example 3

Following the procedure described in the example 1, d-Damascone was encapsulated and placed into a liquid detergent (HDL1) together with some Jaguar C13S to get a perfume concentration of 0.75%. This formulation was then compared to a liquid detergent only containing 1.5% free perfume.

| | Microcapsules Dv 0.5 (μm) | Results wet | Results after 1 days | Results after 2 days | Results after 3 days |
| --- | --- | --- | --- | --- | --- |
| Example 3 | 5.2 | 5/9 | 30/36 | 28/36 | 24/35 |

When the towels were wet or after 3 days of storage the panellists recognised that the perfume intensity was higher when the perfume was encapsulated.

Example 4

Following the procedure described in the example 1, d-Damascone was encapsulated and placed into a liquid detergent (HDL1) together with some Jaguar C13S to get a perfume concentration of 0.75%. This formulation was then compared to a liquid detergent only containing 0.75% free perfume.

| Microcapsules Dv 0.5 (μm) | Results wet | after 1 day | after 2 days | after 3 days | after 6 days | after 7 days | after 8 days | after 9 days | after 10 days |
|---|---|---|---|---|---|---|---|---|---|
| 3.5 | 2/3 | 10/10 | 12/12 | 12/12 | 13/13 | 13/13 | 11/11 | 7/9 | 13/15 |

When the towels were wet and even after 10 days of storage the panellists recognised that the perfume intensity was higher when the perfume was encapsulated.

Example 5

Following the procedure described in the example 1, d-Damascone was encapsulated and placed into a rinse fabric softener to get a perfume concentration of 1.5%. This formulation was then compared to a rinse fabric softener only containing 1.5% of free perfume.

| Microcapsules Dv 0.5 (μm) | Results wet | Results after 1 day | Results after 2 days | Results after 3 days | Results after 6 days | Results after 7 days | Results after 8 days | Results after 9 days |
|---|---|---|---|---|---|---|---|---|
| 5.2 | 5/6 | 5/6 | 7/7 | 8/8 | 7/7 | 10/10 | 6/6 | 9/9 |

Clearly when delivered from a RCFS the encapsulated perfume was more intense than when free in the formulation.

Example 6

Following the procedure described in the example 1, d-Damascone was encapsulated and placed into a rinse fabric softener to get a perfume concentration of 0.5%. This formulation was then compared to a rinse fabric softener only containing 1% of free perfume.

| Microcapsules Dv 0.5 (μm) | Results wet | After 1 day | After 2 days | After 3 days | After 6 days | After 7 days | After 8 days | After 9 days | After 10 days | After 13 days | After 14 days |
|---|---|---|---|---|---|---|---|---|---|---|---|
| 5.2 | 0/4 | 10/10 | 9/9 | 12/12 | 8/8 | 9/9 | 8/9 | 6/6 | 8/9 | 5/8 | 6/6 |

After 14 days 6 panellists out of 6 recognised that the intensity of the encapsulated perfume was higher than the free perfume even if the perfume level initially present was decreased by a factor of 2.

Example 7

Following the procedure described in the example 1, "Fraicheur des Sommets" (from Mane Company) was encapsulated and placed into a rinse fabric softener to get a perfume concentration of 1.5%. This formulation was then compared to a rinse fabric softener only containing 1.5% of free perfume.

| Microcapsules Dv 0.5 (μm) | Results wet | Results after 1 day | Results after 2 days | Results after 3 days | Results after 6 days | Results after 7 days | Results after 8 days | Results after 9 days |
|---|---|---|---|---|---|---|---|---|
| 3.7 | 2/5 | 7/7 | 5/5 | 6/6 | 5/6 | 7/8 | 9/9 | 9/9 |

Here again encapsulation preserved the perfume intensity for more than 9 days.

Comparative Example 1

Following the procedure described in the example 1, d-Damascone was encapsulated to obtain larger particle size by using a mixer IKA Eurostar Digital at 2000 rpm instead of a rotor/stator mixer IKA Ultra-Turax T 25 Basic.

The encapsulated d-Damascone was placed into a liquid detergent (HDL1) together with some Jaguar C13S to get a perfume concentration of 0.75%. This formulation was then compared to a liquid detergent only containing 0.75% free perfume.

| Microcapsules Dv 0.5 (μm) | Results wet | Results after 1 day | after 2 days | after 3 days | after 6 days | after 7 days | after 8 days | after 9 days |
|---|---|---|---|---|---|---|---|---|
| 30 | 2/5 | 5/7 | 5/7 | 7/11 | 6/8 | 5/10 | 3/7 | 4/8 |

With such large microcapsules, the panellists hardly recognise that the perfume intensity is higher than with free perfume. In this case, the advantages brought by the encapsulation process are very low when balanced with the efforts and costs linked to the encapsulation process.

In the following examples 8 to 12 and Comparative Example 2 the same experiments were carried out but after 4 weeks of storage of the fully formulated liquid detergent or rinse cycle fabric softener at 40 C.

Example 8

Following the procedure described in the example 1, d-Damascone was encapsulated and put into a liquid detergent (HDL1) together with some Jaguar C13S to get a perfume concentration of 1.5%. This formulation was then compared to a liquid detergent only containing 1.5% free perfume.

| Microcapsules Dv 0.5 (μm) | Results wet | after 1 day | after 2 days | after 3 days | after 6 days | after 7 days | after 8 days | after 9 days | after 10 days |
|---|---|---|---|---|---|---|---|---|---|
| 5.2 | 3/3 | 7/7 | 3/5 | 1/5 | 4/6 | 4/6 | 3/5 | 8/8 | 8/8 |

After 4 weeks storage at 40 C the performance was kept.

Example 9

Following the procedure described in the example 1, "Fraicheur des Sommets" was encapsulated and put into a liquid detergent (HDL1) together with some Jaguar C13S to get a perfume concentration of 0.4%. This formulation was then compared to a liquid detergent only containing 0.4% free perfume.

| Microcapsules Dv 0.5 (μm) | Results wet | Results after 1 days | Results after 2 days | Results after 3 days | Results after 6 days |
|---|---|---|---|---|---|
| 3.7 | 3/4 | 1/7 | 8/9 | 4/7 | 4/6 |

After 4 weeks storage at 40 C the performance was kept.

Example 10

Following the procedure described in the example 1, d-Damascone was encapsulated and put into a rinse fabric softener to get a perfume concentration of 1.5%. This formulation was then compared to a rinse fabric softener only containing 1.5% of free perfume.

| Microcapsules Dv 0.5 (μm) | Results wet | after 1 day | after 2 days | after 3 days | after 6 days | after 7 days | after 8 days |
|---|---|---|---|---|---|---|---|
| 5.2 | 1/4 | 8/9 | 6/6 | 9/9 | 4/8 | 5/7 | 6/7 |

After 4 weeks storage at 40 C in a rinse cycle fabric softener the performance was kept.

Example 11

Following the procedure described in the example 1, "Fraicheur des Sommets" was encapsulated and put into a rinse fabric softener to get a perfume concentration of 1.5%. This formulation was then compared to a rinse fabric softener only containing 1.5% of free perfume.

| Microcapsules Dv 0.5 (μm) | Results wet | Results after 1 day | Results after 2 days | Results after 3 days | Results after 6 days | Results after 7 days | Results after 14 days |
|---|---|---|---|---|---|---|---|
| 3.7 | 2/4 | 2/4 | 5/7 | 1/3 | 3/4 | 2/4 | 7/7 |

Example 12

Following the procedure described in the example 1, d-Damascone was encapsulated and put into a liquid detergent (HDL1) together with some Jaguar C13S to get a perfume concentration of 0.75%. This formulation was then compared to a liquid detergent only containing 0.75% free perfume.

| Microcapsules Dv 0.5 (μm) | Results wet | after 1 day | after 2 days | after 3 days | after 6 days | after 7 days | after 8 days | after 9 days |
|---|---|---|---|---|---|---|---|---|
| 3.9 | 5/5 | 7/7 | 6/6 | 9/10 | 7/8 | 10/11 | 9/9 | 7/9 |

After 4 weeks storage at 40 C the good performances were kept.

Comparative Example 2

Following the procedure described in the example 1, d-Damascone was encapsulated to obtain larger particle size by using a mixer IKA Eurostar Digital at 2000 rpm instead of a rotor/stator mixer IKA Ultra-Turax T 25 Basic.

The encapsulated perfume was put into a liquid detergent (HDL1) together with some Jaguar C13S to get a perfume concentration of 0.75%. This formulation was then compared to a liquid detergent only containing 0.75% free perfume.

| Microcapsules Dv 0.5 (μm) | Results wet | Results after 1 day | after 2 days | after 3 days | after 6 days | after 7 days |
|---|---|---|---|---|---|---|
| 30 | 3/4 | 7/12 | 9/13 | 4/5 | 3/11 | 7/12 |

In this HDL application, the performances obtained with the large microcapsules of Comparative Example 2 are significantly lower than the performances obtained with the small microcapsules of Example 12, as can be seen after 1 day, 6 days and 7 days.

Example 13

Shower Gel

| | | Wt. % | |
|---|---|---|---|
| Ingredient | INCI name | Pure perfume | Encapsulated perfume |
| Phase A | | | |
| Empicol ESB 3 | Sodium Laureth Sulfate | 30 | 30 |
| Oramix NS 10 | Decyl glucoside | 5 | 5 |
| Amonyl 380BA | Cocamidopropyl Betaine | 10 | 10 |

-continued

| | | Wt. % | |
|---|---|---|---|
| Ingredient | INCI name | Pure perfume | Encapsulated perfume |
| Brij 30 | Laureth-4 | 2 | 2 |
| Water | | 50.3 | 49.23 |

-continued

| | | Wt. % | |
|---|---|---|---|
| Ingredient | INCI name | Pure perfume | Encapsulated perfume |
| Glydant Plus liquid | DMDM Hydantoin and Iodopropylbutylcarbamate | 0.2 | 0.2 |
| Phase B | | | |
| Sepigel 305 | Polyacrylamide and C13-14 Isoparaffin and Laureth-7 | 2 | 2 |
| Phase C | | | |
| Microcapsules | | / | 1.57 |
| Perfume Fraicheur des sommets | | 0.5 | / |
| Total | | 100 | 100 |

Process
1. Mix phase A ingredients together until all ingredients are completely dissolved
2. Add phase B ingredient with mixing.
3. Add perfume or silcap with slow mixing.

The microcapsules had a particle size Dv 0.5 of 4.3 micrometer.

A panel test (9 people) was done with as basic shower gel at 0.5% of perfume (Mane—Fraîcheur des sommets). The panellists were asked to wash one arm with the control shower gel (free perfume) and the other arm with the shower gel containing Core-Shell. Then panellists had to record the arm with the strongest fragrance directly after washing (wet), after 2 min, after 30 min and then every hour (till they don't smell anything). The results showed statistical differences for wet, and after 1 and 2 hours:

Directly after washing (wet): 7/9 panellists for the control shower gel (99% of confidence)

After 1 h, 7/9 panellists for the shower gel with encapsulated perfume (99% of confidence)

After 2 h, 6/9 panellists for the shower gel with encapsulated perfume (95% of confidence)

These results showed that first the free perfume was the strongest but very soon the encapsulated fragrance gives better results.

Example 14

35.01 g of d-Damascone (BLH) was emulsified in 64.39 g water containing 0.20 g Pareth-3 nonionic polyethylene glycol lauryl ether surfactant and 0.11 g cetyl trimethyl ammonium chloride (CTAC) cationic surfactant. The coarse emulsion was emulsified by a rotor/stator mixer IKA Ultra-Turax T 25 Basic at 13500 rpm during 90 seconds. 5% TEOS was added to the emulsion while stirring to form a coarse emulsion of microcapsules. Microcapsules of average volume particle size (Dv 0.5) 21.6 microns (μm) were produced in suspension and the shell thickness was 134 nm.

The suspension was added and mixed with propeller at 300 rpm during 30 minutes to 55 g of a heavy liquid detergent (HDL 1) together with some Jaguar C13S to get an encapsulated d-Damascone concentration of 0.75% (w/w). This composition was left standing at rest for 24 hrs. This formulation was then compared to a liquid detergent only containing 1.5% free perfume.

|  | Microcapsules Dv 0.5 (μm) | Results wet | Results after 1 day | Results after 2 days | Results after 3 days |
| --- | --- | --- | --- | --- | --- |
| Example 14 | 21.6 | 0/5 | 1/9 | 5/11 | 2/8 |

Dv 0.1 = 12.08 μm
Dv 0.5 = 21.6 μm
Dv 0.9 = 37.3 μm

Example 15

35.01 g of d-Damascone (BLH) was emulsified in 64.39 g water containing 0.20 g Pareth-3 nonionic polyethylene glycol lauryl ether surfactant and 0.11 g cetyltrimethyl ammonium chloride (CTAC) cationic surfactant. The coarse emulsion was emulsified by a rotor/stator mixer IKA Ultra-Turax T 25 Basic at 13500 rpm during 90 seconds. 5% TEOS was added to the emulsion while stirring to form a coarse emulsion of microcapsules. Microcapsules of average volume particle size (Dv 0.5) 7.6 microns (μm) were produced in suspension and the shell thickness was 47 nm.

The suspension was added and mixed with propeller at 300 rpm during 30 minutes to 55 g of a heavy liquid detergent (HDL 1) together with some Jaguar C13S to get an encapsulated d-Damascone concentration of 0.75% (w/w). This composition was left standing at rest for 24 hrs. This formulation was then compared to a liquid detergent only containing 1.5% free perfume.

|  | Microcapsules Dv 0.5 (μm) | Results wet | Results after 1 day | Results after 2 days | Results after 3 days |
| --- | --- | --- | --- | --- | --- |
| Example 15 | 7.6 | 0/5 | 6/9 | 7/12 | 6/8 |

Dv 0.1 = 4.5 μm
Dv 0.5 = 7.6 μm
Dv 0.9 = 12.5 μm

Comparing examples 14 and 15 showed that high microcapsule size (21.6 micrometer) is associated with a lower amount of panellist capable to pick up the towels that were treated with the delta damascone containing microcapsules. In other words these results confirmed that the preferable microcapsule sizes are in the lower size range, preferably less than 20 micrometer.

Example 16

Sol-Gel Process 35.01 g of d-Damascone (BLH) was mixed with 5 gr of TEOS and emulsified in 64.39 g water containing 0.20 g Pareth-3 nonionic polyethylene glycol lauryl ether surfactant and 0.11 g cetyl trimethyl ammonium chloride (CTAC) cationic surfactant. The coarse emulsion was emulsified by a rotor/stator mixer IKA Ultra-Turax T 25 Basic at 13500 rpm during 90 seconds. Microcapsules of average volume particle size (Dv 0.5) 5.0 microns (μm) were produced in suspension and the shell thickness was 31 nm.

The suspension was added and mixed with propeller at 300 rpm during 30 minutes to 55 g of a heavy liquid detergent (HDL 1) together with some Jaguar C13S to get an encapsulated d-Damascone concentration of 0.75% (w/w). This composition was left standing at rest for 24 hrs. This formulation was then compared to a liquid detergent only containing 1.5% free perfume.

|  | Microcapsules Dv 0.5 (μm) | Results wet | Results after 1 days | Results after 2 days | Results after 3 days |
| --- | --- | --- | --- | --- | --- |
| Example 16 | 5.0 | 0/6 | 8/12 | 3/8 | N.A. |

Dv 0.1 = 3.4 μm
Dv 0.5 = 5.0 μm
Dv 0.9 = 32.3 μm

This example showed that sol-gel process were the active ingredient is directly emulsified with TEOS gives poorer performances than a core-shell process were the active ingredient is emulsified before TEOS incorporation.
Comparative Example Sol Gel Process as in US 2004/0256748 A1
Of 116 g of TEOS, first 16 g was slowly added to 0.01M aqueous solution of HCl 10 g for 18 min. and the remaining was added for 6 min. The reaction mixture was stirred for 72 min to obtain a clear solution. The later was evaporated at a temperature of 50° C. to remove ethanol produced by a biproduct during the reaction. The resulting solution was a clear viscous precursor solution for lipophilic core material. 20 part per weight of delta damascone as a core material was dissolved in the precursor solution. 1 part by weight of triton X-100 in a separate container was stirred at a rate of about 1000 rpm, 20 part per weight of the emulsion solution prepared above compared to the aqueous solution was added therein to produce W/O emulsion. After the reaction mixture was reacted for 10 minutes and left for 2 hours, particle precipitated at the bottom were filtered and add and mixed with propeller at 300 rpm during 30 minutes to a heavy liquid detergent (HDL 1) together with some Jaguar C13S to get an encapsulated d-Damascone concentration of 0.75% (w/w). This composition was not homogeneous since rapid aggregates precipitated at the bottom of the HDL preparation.
This unstable preparation cannot be tested properly.
Microcapsules made by such sol gel process were not compatible with a detergent containing composition. Therefore an accurate performance measurement was not possible.

Particle size distribution was not measured because of heterogeneous bend and crystal particle.

The invention claimed is:

1. A fragrance carrier system comprising an encapsulated fragrance composition, wherein the fragrance composition contains an emulsion of a fragrance compound in an aqueous medium, and the fragrance composition is encapsulated within a shell which is an emulsion polymerisation product of a tetraalkoxysilane and the shell has a mean diameter size which is lower than 30 micrometer, obtained by forming first an aqueous emulsion containing the fragrance composition, then adding the tetraalkoxysilane in a continuous phase under shear and conducting an ex situ polymerisation.

2. The fragrance carrier system according to claim 1, wherein the shell has a mean diameter size lower than 20 micrometer.

3. The fragrance carrier system according to claim 1, wherein the shell has a mean diameter size of at least 0.5 micrometer.

4. The fragrance carrier system according to claim 1, wherein the shell has a mean diameter size between 1 and 10 micrometer.

5. The fragrance carrier system according to claim 1, wherein the shell has a mean diameter size between 1.5 and 7 micrometer.

6. A surfactant containing composition containing the fragrance carrier system according to claim 1.

7. The surfactant composition according to claim 6, which is a rinse-off composition.

8. The surfactant composition according to claim 6, wherein the surfactant composition is selected from a fabric softener, liquid laundry detergent, rinse added product, drier-added fabric softener product, ironing added product, hair conditioner, shampoo, soap, dish-washing product and shower gel.

9. The surfactant composition according to claim 6, wherein the surfactant composition contains a deposition aid material.

10. The surfactant composition according to claim 9, wherein the deposition aid material is a cationic guar gum derivative.

11. A process to deliver a fragrance to a substrate, wherein the substrate is treated by a surfactant composition according to claim 6, the surfactant composition is washed off and the fragrance is progressively released.

12. The fragrance carrier system according to claim 1, wherein the shell is an ex situ emulsion polymerisation product of the tetraalkoxysilane.

13. The surfactant composition according to claim 9, wherein the deposition aid material is selected from at least one of: quaternary ammonium compounds, polyvinyl amines, polyalkyleneimines, and poly-quaternary ammonium compounds.

* * * * *